US012734265B2

(12) United States Patent
Wong et al.

(10) Patent No.: US 12,734,265 B2
(45) Date of Patent: Sep. 15, 2026

(54) WATER-SOLUBLE PHOTOSENSITIVE COMPOSITION OF PHOTODYNAMIC ENVIRONMENTAL DISINFECTION AND METHOD OF ENVIRONMENTAL DISINFECTION BY USING THE SAME

(71) Applicant: NATIONAL CHENG KUNG UNIVERSITY, Tainan City (TW)

(72) Inventors: Tak-Wah Wong, Tainan City (TW); Chun-Keung Yu, Tainan City (TW); Ming-Yeng Lin, Tainan City (TW)

(73) Assignee: NATIONAL CHENG KUNG UNIVERSITY, Tainan City (TW)

( * ) Notice: Subject to any disclaimer, the term of this patent is extended or adjusted under 35 U.S.C. 154(b) by 462 days.

(21) Appl. No.: 18/351,532

(22) Filed: Jul. 13, 2023

(65) Prior Publication Data

US 2024/0181106 A1 Jun. 6, 2024

(30) Foreign Application Priority Data

Dec. 5, 2022 (TW) ................................. 111146535

(51) Int. Cl.
*A61L 2/22* (2006.01)
*A61L 9/14* (2006.01)

(52) U.S. Cl.
CPC .................. *A61L 2/22* (2013.01); *A61L 9/14* (2013.01)

(58) Field of Classification Search
CPC .......... A61L 2/22; A61L 9/14; A61L 2103/75; A61L 2202/11; A61L 2209/211; A61L 2/084; A61L 2/208; A61L 9/18; A61L 2101/44
See application file for complete search history.

(56) References Cited

U.S. PATENT DOCUMENTS

| | | | | |
|---|---|---|---|---|
| 8,685,466 B2 * | 4/2014 | Piergallini | ............. | A61K 8/498 604/20 |
| 12,589,175 B1 * | 3/2026 | Whitaker | .................. | A61L 2/22 |
| 2016/0067149 A1 * | 3/2016 | Kishen | .................... | A61P 31/02 424/44 |

FOREIGN PATENT DOCUMENTS

| | | |
|---|---|---|
| CN | 1457894 A | 11/2003 |
| CN | 102802676 A | 11/2012 |
| CN | 109715777 A | 5/2019 |

(Continued)

OTHER PUBLICATIONS

McCullagh, C and Robertson, P.K. Environ. Sci Technol. 2006, 40, 2421-2425 (Year: 2006).*

*Primary Examiner* — Regina M Yoo
(74) *Attorney, Agent, or Firm* — McBee Moore & Vanik IP, LLC

(57) ABSTRACT

The present invention is appertaining to a water-soluble photosensitive composition of photodynamic environmental disinfection and method of environmental disinfection by using the same. In this method, a short-term atomization step and a white light irradiation step with a low light dose are performed on the water-soluble photosensitive composition composed of water, low-concentration methylene blue and hydrogen peroxide to obtain photoactivated atomized particles, which can be performed in a sequential or simultaneous manner. The obtained photoactivated atomized particles can effectively inhibit the pathogenicity and/or the infectivity of viruses in the environment, and therefore, be applied to the method of photodynamic environmental disinfection.

16 Claims, 10 Drawing Sheets

(56) References Cited

FOREIGN PATENT DOCUMENTS

| | | | | |
|---|---|---|---|---|
| CN | 113519550 | A | 10/2021 | |
| KR | 101436126 | B1 * | 9/2014 | ............... A61K 8/29 |
| TW | 202029994 | A | 8/2020 | |
| WO | WO-2009123575 | A1 * | 10/2009 | ............. A61P 43/00 |

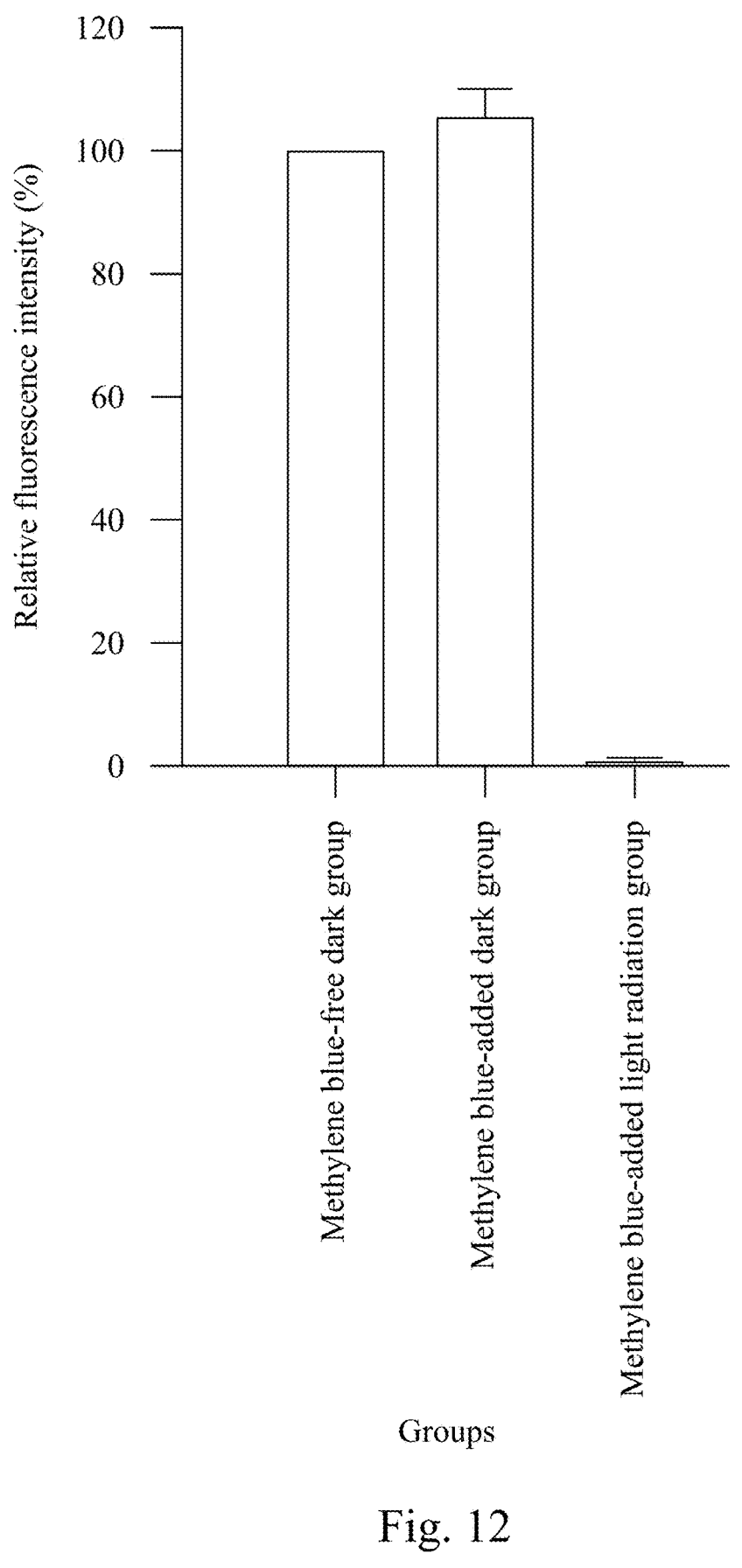

* cited by examiner 120
100
80
60
40
20
0

Relative fluorescence intensity (%)

Methylene blue-free dark group
Methylene blue-added dark group
Methylene blue-added light radiation group Groups

Fig. 12

WATER-SOLUBLE PHOTOSENSITIVE COMPOSITION OF PHOTODYNAMIC ENVIRONMENTAL DISINFECTION AND METHOD OF ENVIRONMENTAL DISINFECTION BY USING THE SAME

RELATED APPLICATION

This application claims priority to an earlier Taiwan Application Serial Number TW 111146535, filed Dec. 5, 2022, which is incorporated herein by reference in its entirety.

A sequence listing is being submitted herein as an xml text file with the name "SP-5772-US_SEQLIST.xml", created on Jun. 12, 2023, with a file size of 807.5 bytes.

BACKGROUND

Field of Invention

The present disclosure relates to a composition of environmental disinfection, in particular to a water-soluble photosensitive composition of photodynamic environmental disinfection and a method of environmental disinfection by using the same.

Description of Related Art

In modern life, transportation of people and goods has become faster and more convenient, but it has also accelerated the spread of pathogens. Waves of serious infectious disease outbreaks in recent years show that infectious diseases still threaten people's lives. The outbreaks of infectious diseases transmitted by airborne and/or contact, such as outbreaks of severe special infectious pneumonia in 2019 (coronavirus disease 2019, COVID-19), have highlighted the need for environmental disinfection.

Known methods of environmental disinfection include chemical cleaning, fumigation and/or light irradiation, in which the chemical cleaning includes the use of chemicals (e.g., surfactants, bleach, alcohol, hydrogen peroxide, peracetic acid and quaternary ammonium salt) to clean an environmental surface, and the fumigation includes exposing an environmental surface to ethylene oxide (EtO) and/or ozone, and the light irradiation includes exposing an environmental surface to short-wavelength light (e.g., gamma rays and/or UV light). However, the above conventional methods may harm the human body and/or the environment.

Photodynamic therapy (referred to as PDT) is a kind of phototherapy to give a non-toxic photosensitizer to a whole body or an affected part of a specific small area of the body, and then exposes the body to a specific wavelength of light, in which the photosensitizer absorbs enough light dose to generate reactive oxygen species (ROS) and/or singlet oxygen, which is phototoxic to cancer cells or pathogens in the specific small area to achieve a therapeutic effect. However, for large-scale environmental disinfection, in order to generate a sufficient dose of ROS and/or singlet oxygen, a sufficient dose of the photosensitizer, a high light dose, and the specific wavelength of light need to be provided, which increases the difficulty to apply the photosensitizer for environmental disinfection.

Therefore, there is an urgent need for a method and a composition of photodynamic environmental disinfection to solve the above issues.

SUMMARY

An aspect of the present disclosure is to provide a method of photodynamic environmental disinfection, which is to perform an atomization step and a light irradiation step on a water-soluble photosensitive composition to obtain photoactivated atomized particles, which are applied to a surface of an object and/or air in the application environment, thereby reducing the pathogenicity and/or the infectivity of viruses on the surface of the object and/or the air in the environment.

Another aspect of the present invention is to provide a water-soluble photosensitive composition of photodynamic environmental disinfection, which is consisting of methylene blue, hydrogen peroxide and water.

The other aspect of the present invention is to provide a method of environmental disinfection with a water-soluble photosensitive composition, in which after an atomization step and a light irradiation step are performed on a water-soluble photosensitive composition, obtained photoactivated atomized particles can reduce the pathogenicity and/or the infectivity of a surface of an object and/or air of viruses in the environment.

According to the above aspect of the present invention, a method of photodynamic environmental disinfection is provided. First, an atomization step is performed on a water-soluble photosensitive composition to obtain atomized particles in space. The water-soluble photosensitive composition may be consisting of methylene blue of more than 0 mM and equal to or less than 50 mM, hydrogen peroxide ($H_2O_2$) of more than 0 wt % to 1 wt %, and a balanced amount of water.

Next, a light irradiation step using white light of 0.01 $J/cm^2$ to 300 $J/cm^2$ is performed on the atomized particles for a time of irradiation to obtain photoactivated atomized particles. The photoactivated atomized particles are then applied to a surface of an object and/or air of the space, in which compared to the surface of the object and/or the air of the space where the photoactivated atomized particles are not applied, the pathogenicity and/or the infectivity of viruses on the surface of the object and/or in the air of the space where the photoactivated atomized particles are applied is reduced by at least 99.99%.

In one embodiment of the present invention, the atomization step is performed at a rate of 0.1 mL to 150 mL per minute. In one embodiment of the present invention, the atomization step is performed for 1 second to 300 seconds. In one embodiment of the present invention, a particle size of each of the atomized particles is 0.1 μm to 100 μm. In one embodiment of the present invention, a total volume ratio of the space to each of the atomized particles is 1:0.0001 to 1:0.01. In one embodiment of the present invention, a light source of white light is selected from the group consisting of natural light, a light-emitting diode, a fluorescent lamp, a halogen lamp, an incandescent lamp, a laser, and any combination thereof. In one embodiment of the present invention, a wavelength of the white light comprises 400 nm to 760 nm. In one embodiment of the present invention, the viruses are selected from the group consisting of Flaviviridae, Fiersviridae, Coronaviridae and any combination thereof. In one embodiment of the present invention, the viruses are selected from the group consisting of hepatitis C virus (HCV), dengue virus (DENV), MS2 bacteriophage, severe acute respiratory syndrome coronavirus 2 (SARS-COV-2) and any combination thereof.

The method of photodynamic environmental disinfection of the present invention uses a water-soluble and low-dose photosensitizer, so it is not easy to remain and endanger human body and/or environment. Secondly, applying the water-soluble photosensitive composition to the method of photodynamic environmental disinfection can effectively inhibit the pathogenicity and/or the infectivity of viruses on the surface of the object and/or the air in the environment by using short-term and low-dose white light, which does not need to use the specific wavelength of light and has low requirements for light source equipment, and thus can be widely used.

BRIEF DESCRIPTION OF THE DRAWINGS

In order to make the aforementioned and other purposes, features, advantages and embodiments of the present invention more obvious and understandable, the detailed description of the accompanying drawings is as follows:

FIG. 12 is a histogram of quantified relative fluorescence intensity of host cells in FIG. 9B, FIG. 10B and FIG. 11B.

DETAILED DESCRIPTION

Figure 1:
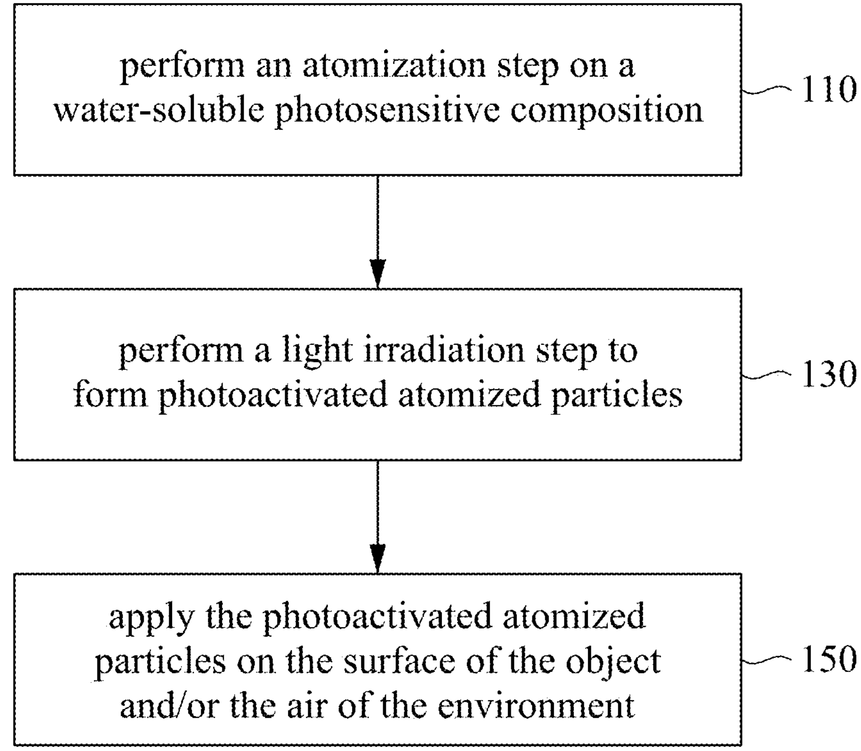
FIG. 1 is a flowchart illustrating a method of photodynamic environmental disinfection according to an embodiment of the present invention.

As mentioned above, the present invention provides a water-soluble photosensitive composition of photodynamic environmental disinfection, a method of environmental disinfection of the same, in which after the water-soluble photosensitive composition is subjected to an atomization step and a light irradiation step, the obtained photoactivated atomized particles have a good environmental disinfection efficacy.

The aforementioned water-soluble photosensitive composition may be, for example, composed of a photosensitizer, hydrogen peroxide ($H_2O_2$) and water. The type of the photosensitizer is not particularly limited, preferably a water-soluble photosensitizer, which may include but not limited to water-soluble photosensitizers commonly used in photodynamic therapy such as methylene blue (MB), crystal violet, toluidine blue, acridine orange, eosin, rose bengal and/or indocyanine green, etc. If an oil-soluble photosensitizer is used, such as 8-methoxypsoralen, it is necessary to use an organic solvent to dissolve the photosensitizer, which harms the human body and/or the environment. Therefore, the present disclosure excludes the use of the oil-soluble photosensitizer.

Based on 100 wt % of the water-soluble photosensitive composition, the content of the photosensitizer may be, for example, greater than 0 mM and equal to or less than 50 mM. If the content of the photosensitizer is too high, the production cost increases significantly without significantly improving the environmental disinfection efficacy of the photoactivated atomized particles obtained by a prepared water-soluble photosensitive composition. Secondly, the photosensitizer usually has a color. If the content of the photosensitizer is too high, the color of the prepared water-soluble photosensitive composition is too dark, which blocks the penetration of light in the subsequent light irradiation step, thereby affecting the environmental disinfection efficacy. Moreover, the obtained photoactivated atomized particles may adhere and stain the surface of an object (e.g., cloth and/or paper). Although the stains will gradually recede after exposure to light, they will still cause inconvenience in use. In a specific example, the content of methylene blue in the water-soluble photosensitive composition is 0.001 mM to 10 mM, 0.001 mM to 1 mM, or 0.002 mM to 0.004 mM. It is noted that a maximum safe dose of methylene blue administered to a human is 2 mg/kg/single dose, and it is safe to administer methylene blue to a 60 kg-weight adult at a single dose of 120 mg every 4 hours, not exceeding 7 mg/kg daily. Therefore, tens of thousands of liters of the water-soluble photosensitive composition are required to exceed the maximum safe dose of methylene blue, which means that the dosage of methylene blue used in the water-soluble photosensitive composition is indeed extremely low.

Based on 100% of the water-soluble photosensitive composition, the content of hydrogen peroxide may be, for example, greater than 0 wt % to 1 wt %. Hydrogen peroxide is a strong oxidant, so if the content of hydrogen peroxide is too high, photoactivated atomized particles obtained by a prepared water-soluble photosensitive composition may irritate the mucous membranes of the skin, the eyes and/or the respiratory tract of a human body after contacting the human body. However, if the content of hydrogen peroxide is too low, an environmental disinfection efficacy of the photoactivated atomized particles obtained by the prepared water-soluble photosensitive composition is not good. In a specific example, the content of hydrogen peroxide may be, for example, 0.025% to 0.035 wt %, preferably 0.03 wt %.

Hydrogen peroxide is a strong oxidizing agent, which is easily degraded after contacting air, so a stabilizer may be optionally added to a commercially available 3% hydrogen peroxide product. In some embodiments, based on 100% of hydrogen peroxide, hydrogen peroxide may selectively include 0.05 wt % to 1.00 wt % of the stabilizer to improve the stability of hydrogen peroxide. The type of the stabilizer is not particularly limited and, for example, may be selected from the group consisting of acetaminophen, acetanilide, phenacetin, poly (vinyl alcohol) (PVA) and combinations thereof, or other commercially available stabilizers contained in hydrogen peroxide for wound disinfection. The content of hydrogen peroxide in the water-soluble photosensitive composition of the present invention is low, so the aforementioned stabilizer may not be added or may be selectively added to the water-soluble photosensitive composition.

The aforementioned water-soluble photosensitive composition may be applied to the method of photodynamic environmental disinfection. Please refer to FIG. 1, which is a flowchart illustrating a method 100 of photodynamic environmental disinfection according to an embodiment of the present invention. As shown in Step 110 of FIG. 1, an atomization step is performed on the water-soluble photosensitive composition to obtain atomized particles in space. The equipment used in the atomization step is not particularly limited, and may be, for example, an atomizer or a nebulizer. In a specific example, an ultrasonic atomizer is used in the atomization step to obtain the atomized particles with a particle size of 0.1 μm to 100.0 μm, such as 0.5 μm to 50 μm, so as to increase the total surface area of the atomized particles.

The rate of the atomization step is not particularly limited, and may be adjusted according to requirements, for example, according to the time of the atomization step. The rate of the atomization step may be, for example, 0.1 mL to 150 mL per minute, such as 15 mL to 25 mL per minute, or 20 mL. If the rate of the atomization step is too slow, atomized particles provided in a short period (e.g., 50 seconds to 100 seconds) are insufficient to fill the targeted space for an effective environmental disinfection. If the rate of the atomization step is too fast, the production cost significantly increases without significantly improving the environmental disinfection efficacy.

Next, as shown in Step 130 of FIG. 1, the atomized particles are irradiated with visible light (e.g., red light), infrared rays or white light for a time of irradiation to obtain photoactivated atomized particles, in which a light dose may be, for example, 0.01 $J/cm^2$ to 300 $J/cm^2$, or 0.5 $J/cm^2$ to 50 $J/cm^2$, or 2.5 $J/cm^2$ to 20 $J/cm^2$. If the light dose of visible light, infrared rays or white light is less than the above range, an environmental disinfection efficacy is not good. If the light dose of the visible light, infrared ray or white light is greater than the above range, production cost significantly increased without significantly improving the environmental disinfection efficacy.

The aforementioned white light is a continuous spectrum or a continuous spectrum composed of light of at least two colors (wavelengths). In some embodiments, the wavelengths of white light include 400 nm to 760 nm. In some embodiments, the white light may be, for example, composed of red light (with wavelengths of 630 nm to 760 nm), green light (with wavelengths of 495 nm to 570 nm) and blue light (with wavelengths of 450 nm to 475 nm). In some other embodiments, the white light may include infrared rays, in which the wavelength of the infrared rays may be greater than 760 nm to 1 mm, for example. In some embodiments, the white light is composed of light of complementary colors, such as red light and cyan light (with wavelengths of 475 nm to 495 nm). Compared to the conventional photodynamic therapy that needs specific light sources to provide a high light power with a specific wavelength, the aforementioned method of photodynamic environmental disinfection requires low light energy and does not need to be limited to a specific wavelength, so the requirements for specific light sources are relatively low. The type of white light source is not particularly limited and, for example, may be selected from the group consisting of natural light, a light-emitting diode (LED), a fluorescent lamp, a halogen lamp, an incandescent lamp, and any combination thereof.

The white light intensity and the time of irradiation on the atomized particles are not particularly limited and depend on the lighting equipment and the required light dose. In some embodiments, the white light intensity on the atomized particles may be, for example, 0.1 $mW/cm^2$ to 70 $mW/cm^2$, 30 $mW/cm^2$ to 70 $mW/cm^2$, 20 $mW/cm^2$ to 40 $mW/cm^2$, or 60 $mW/cm^2$ to 70 $mW/cm^2$. In one embodiment, the white light intensity is 70 $mW/cm^2$ and the time of irradiation is 0.14 seconds to 1.2 hours to provide the atomized particles with a light dose of about 0.01 $J/cm^2$ to 300 $J/cm^2$. In a specific example, the white light intensity is 20 $mW/cm^2$ to 40 $mW/cm^2$ and the time of irradiation is about 1 minute to 2 minutes to provide the atomized particles with a light dose of about 2.5 $J/cm^2$. In a specific example, the white light intensity is 67 $mW/cm^2$ and the time of irradiation is 37 seconds, 2.5 minutes or 5 minutes to provide the atomized particles with a light dose of 2.5 $J/cm^2$, 10 $J/cm^2$ or 20 $J/cm^2$. In another specific example, the white light includes red light with a light intensity of 32.8 $mW/cm^2$ and the time of irradiation is 9 seconds to 19 seconds to provide the atomized particles with the light dose of 0.3 $J/cm^2$ to 0.6 $J/cm^2$.

After the light irradiation step is performed on the atomized particles, the photosensitizer of the atomized particles is activated, so that the obtained photoactivated atomized particles generate active oxygen-containing species, such as singlet oxygen and/or free radicals. Therefore, as shown in Step 150 of FIG. 1, the photoactivated atomized particles applied on the surfaces of the object and/or the airs in the environment have a good environmental disinfection efficacy. It is worth noting that it has been confirmed by in vitro experiments that the atomized particles without hydrogen peroxide that are exposed to the light of a light dose of 0.3 $J/cm^2$ can reduce the pathogenicity and/or the infectivity of the virus by 99.9% (equivalent to 3 logarithms, 3 logs), and the atomized particles without hydrogen peroxide that is exposed to the light of a light dose of 0.6 $J/cm^2$ can reduce the pathogenicity and/or the infectivity of the virus by 99.999999% to 99.9999999% (equivalent to 8 to 9 logarithms, 8 logs to 9 logs). Secondly, it has been confirmed by in vitro experiments that the water-soluble photosensitive composition containing hydrogen peroxide can reduce 40% of the pathogenicity and/or the infectivity of the virus after being subjected to the atomization step but not the light irradiation step. It may be deduced from this that the water-soluble photosensitive composition (containing hydrogen peroxide) of the present invention may reduce the pathogenicity and/or the infectivity of the virus by at least 99.99% after subjected to the light irradiation step with the low dose of the white light.

The term "environment" described herein refers to space for individual activity and/or objects. The location of the space is not particularly limited, and may be, for example, an open, semi-open or closed space, including but not limited to a COVID-19 screening unit, a laboratory entrance, a hospital, a hotel, a ward, a transport vehicle compartment, a classroom, an office, an elevator, a movie theater, a private room, a restaurant and/or an airport. A total volume ratio of the atomized particles to the application space is not limited and may be, for example, 1:0.0001 to 1:0.01, so as to ensure that the atomized particles can be fully in contact with the surface of the object and/or the air in this space, so as to achieve a better environmental disinfection efficacy. In some embodiments, when a volume of the application space is 1 $m^3$, a volume of the water-soluble photosensitive composition of obtaining the atomized particles is 1 mL to 500 mL, or 300 mL to 400 ml (e.g., 358 mL), or 70 mL to 80 mL (e.g., 71.6 mL). In a specific example, when the volume of the water-soluble photosensitive composition of the atomized particles is 1 mL, the volume of the space is 1000 mL to 2000 mL, such as 1397 mL.

The term "environmental disinfection" described herein refers to reducing the infectivity of pathogens on a surface of an object and/or in the air in the environment, which may include but not limited to reducing pathogenicity, infectivity, growth activity and/or quantity. The term "better environmental disinfection efficacy" described herein refers to a reduction of the pathogenicity and/or the infectivity of pathogens on the surface of the object and/or in the air of the environment where the photoactivated atomized particles are applied by at least 99.9% (equivalent to 3 logarithms, 3 logs, the US standard for disinfectants to effectively kill virus) or 99.99% (equivalent to 4 logarithms, 4 logs, the European Union's standard for disinfectants to effectively kill virus) compared to that of pathogens on the surface of the object and/or the air of the environment where the photoactivated atomized particles are not applied. In a preferred embodiment, the pathogenicity and/or the infectivity of pathogens on the surface of the object and/or in the air of the environment where the photoactivated atomized particles are applied is reduced by at least 99.999% (equivalent to 5 logarithms, 5 logs).

The term "pathogenicity" described herein refers to the ability of a pathogen to cause disease in a host, in which a degree of pathogenicity may be expressed by relative viral load and/or virulence. The relative viral load is a percentage of a viral load on the surface of the object and/or the air (hereinafter referred to as the environment) in the space treated with photoactivated atomized particles to a viral load that is untreated, in which the viral load may be quantified, for example, using real-time quantitative polymerase chain reaction (Q-PCR) assessment. The virulence may be evaluated, for example, by the number of lysed bacteria produced in a plaque assay, and the virulence of the virus is represented by the number of plaque-forming units produced per unit volume of a virus solution (PFU/mL).

The term "infectivity" described herein refers to the capability of a pathogen to enter a cell. The method of evaluating infectivity is not particularly limited. For example, a host cell may be infected with a pseudovirus that can express viral spike protein (S protein) and reporter gene, and infectivity may be evaluated by the reporter gene expression level of host cells. The type of the reporter gene is not particularly limited, and may be, for example, green fluorescent protein (GFP), β-galactosidase gene and/or luciferase.

The aforementioned pathogen refers to a pathogenic microorganism or agent, which may include but not limited to misfolded protein (prion), virus, bacteria, fungi and/or protist. According to the structures of viruses, the viruses may be divided into enveloped viruses and non-enveloped viruses. It is worth noting that previous studies have confirmed that compared to the enveloped virus, the non-enveloped virus has a higher tolerance to the method of photodynamic environmental disinfection. It may be deduced from this that if the method of photodynamic environmental disinfection can inhibit the non-enveloped virus effectively, it can inhibit the enveloped virus more effectively.

In some embodiments, the virus may be selected from the group consisting of Flaviviridae, Fiersviridae, Coronaviridae and any combination thereof. In some embodiments, Flaviviridae may include but not limited to hepatitis C virus (HCV) and/or dengue virus (DENV), which are enveloped viruses, and Fiersviridae may include but not limited to bacteriophage MS2, which is a non-enveloped virus, and Coronaviridae may include but not limited to severe acute respiratory syndrome coronavirus 2 (SARS-COV-2), which is an enveloped virus.

It is supplemented that the order of Steps 110, 130 and 150 is only an example, and may be carried out sequentially and/or simultaneously. For example, Step 110 (i.e., the atomization step) and Step 130 (i.e., the light irradiation step) can be carried out simultaneously. In one embodiment, the light irradiation step is performed after the atomized particles are applied to the surface of the object and/or the air in the environment.

The method of photodynamic environmental disinfection of the present invention only needs low doses of methylene blue, hydrogen peroxide and the light source with the low light dose and a non-specific wavelength, and thus can be easily applied in daily life. For example, a spraying device may be provided at the entrance and exit to atomize the water-soluble photosensitive composition to apply the atomized particles on incoming and outgoing objects and/or biological surfaces. Sunlight and/or any artificial white light can be used to perform the light irradiation step on these atomized particles, thereby obtaining the photoactivated atomized particles. In another embodiment, the aforementioned method of photodynamic environmental disinfection may be applied to a portable spraying device, in which the portable spraying device includes a solution device, an atomization device and a light source device, and the solution device is connected to the atomization device, and the light source device is electrically or mechanically connected to the atomization device. The solution device is used to accommodate the water-soluble photosensitive composition, the atomization device is used to atomize the water-soluble photosensitive composition in the solution device to obtain the atomized particles, and the light source device is used to perform the light irradiation step on the atomized particles to obtain the photoactivated atomized particles.

The application of the present invention is described below by several embodiments, but those are not intended to limit the present invention. A person having ordinary skill in the art of the present invention may make various changes and modifications without departing from the spirit and scope of the present invention.

Embodiment 1. Preparation of Water-Soluble Photosensitive Composition

A water-soluble photosensitive composition of Preparation Example 1 was composed of 0.004 mM of methylene blue, 0.03 wt % of hydrogen peroxide and water. A water-soluble photosensitive composition of Preparation Example 2 was composed of 0.004 mM of methylene blue and water (hydrogen peroxide-free).

Embodiment 2. Evaluation of Environmental Disinfection Efficacy of Photoactivated Atomized Particles Obtained by Water-Soluble Photosensitive Composition 1. Build an Experimental Model.

The test was conducted in an airtight box (43 cm×58 cm×28 cm). A 96-well cell culture plate and an ultrasonic atomizer (model: Polar Bear ultrasonic three-head atomizer UT-3, with an atomization rate of 1.2 L/hour) were placed in the airtight box. 0.1 mL of a virus solution was pre-added to each well of the 96-well cell culture plate, in which the virus solution was prepared with sterile phosphate-buffered saline (PBS), and the virus solution contained 108 PFU/mL of the virus. The ultrasonic atomizer was installed in the bottom part of the airtight box, and the water-soluble photosensitive composition was atomized by the ultrasonic atomizer for an atomization time, thereby obtaining atomized particles in the airtight box, and a portion of the atomized particles fell into the virus solution of the 96-well cell culture plate.

Next, the 96-well cell culture plate was taken out and placed 100 cm under a white LED with a light intensity of 67 mW/cm$^2$ measured at the bottom of the 96-well cell culture plate to achieve adequate light dose (hereinafter referred to as the light dose at the bottom of the plate). Next, nucleic acid fragments shown in SEQ ID NO: 1 and SEQ ID NO: 2 were used as an upstream primer and a downstream primer, respectively, so as to detect a viral load of HCV by Q-PCR, and nucleic acid fragments shown in SEQ ID NO: 3 and SEQ ID NO: 4 were used as an upstream primer and a downstream primer, respectively, so as to detect a viral load of DENV by Q-PCR, in which Q-PCR was carried out conventionally without affecting follow-up evaluation, so details were not described.

2. Effects of Light Irradiation Step and Hydrogen Peroxide on Environmental Disinfection Efficacy.

Whether to carry out the light irradiation step (the light dose at the bottom of the plate was 20 J/cm$^2$) and whether to add hydrogen peroxide (the additional amount was 0.03 wt %) in the water-soluble photosensitive composition were the test conditions to evaluate the effects of the light irradiation step and hydrogen peroxide on the environmental disinfection efficacy of the obtained photoactivated atomized particles. A hydrogen peroxide-free dark group was the water-soluble photosensitive composition of Preparation Example 2 (hydrogen peroxide-free) not subjected to the light irradiation step. A hydrogen peroxide-added dark group was the water-soluble photosensitive composition of Preparation Example 1 (containing hydrogen peroxide) not subjected to the light irradiation step. A hydrogen peroxide-free light irradiation group was the water-soluble photosensitive composition of Preparation Example 2 (hydrogen peroxide-free) subjected to the light irradiation step. A hydrogen peroxide-added light irradiation group was the water-soluble photosensitive composition of Preparation Example 1 (containing hydrogen peroxide) subjected to the light irradiation step. The time for the atomization step of the hydrogen peroxide-free dark group, the hydrogen peroxide-added dark group, the hydrogen peroxide-free light irradiation group, and the hydrogen peroxide-added light irradiation group was 150 seconds.

Figure 2:
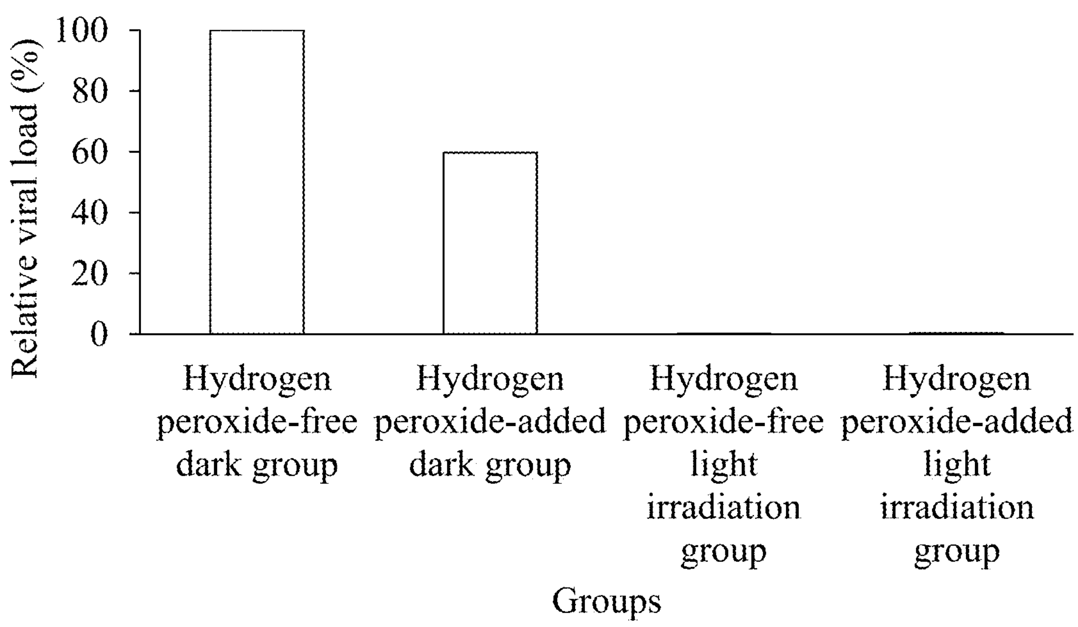
FIG. 2 is a histogram of the relative toxicity to HCV of the atomized particles whether or not photoactivated with a light irradiation step of 20 J/cm$^2$ with/without the addition of hydrogen peroxide according to an embodiment of the present invention.
Figure 3:
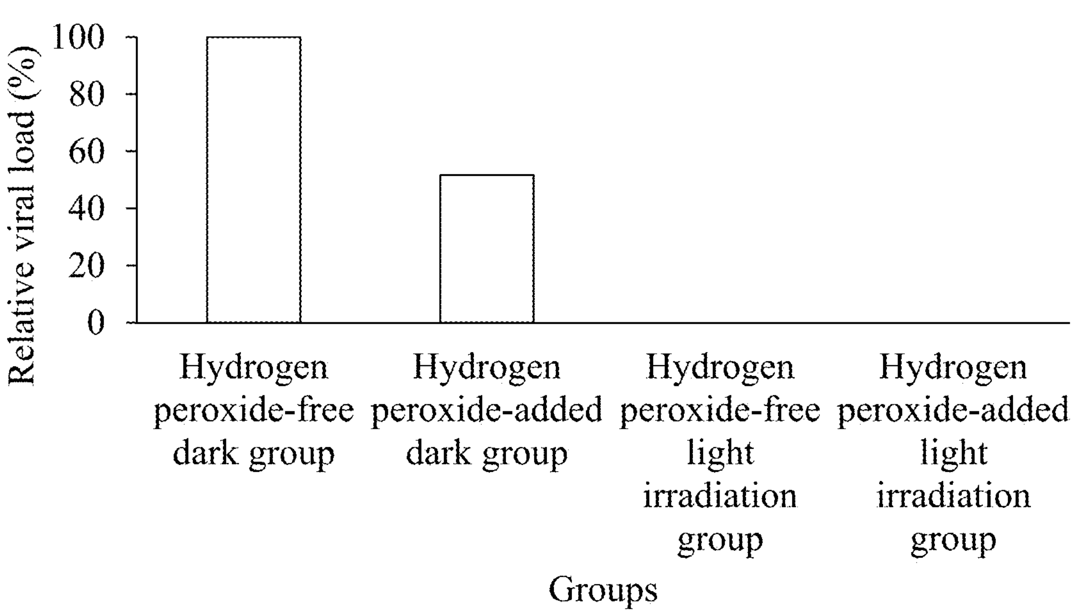
FIG. 3 is a histogram of the relative toxicity to DENV of the atomized particles whether or not photoactivated with a light irradiation step of 20 J/cm$^2$ with/without the addition of hydrogen peroxide according to an embodiment of the present invention.

Please refer to FIG. 2 and FIG. 3, in which FIG. 2 was a histogram of the relative toxicity to HCV of the atomized particles and/or the photoactivated atomized particles subjected to a light irradiation step of 20 J/cm$^2$ or not and added with hydrogen peroxide or not according to an embodiment of the present invention, and FIG. 3 was a histogram of the relative toxicity to DENV of the atomized particles and/or the photoactivated atomized particles subjected to a light irradiation step of 20 J/cm$^2$ or not and added with hydrogen peroxide or not according to an embodiment of the present invention. The horizontal axes of FIG. 2 and FIG. 3 represented the different groups, which were the hydrogen peroxide-free dark group, the hydrogen peroxide-added dark group, the hydrogen peroxide-free light irradiation group, and the hydrogen peroxide-added light irradiation group from left to right, and the vertical axes thereof represented the relative viral load (unit: %), in which the relative viral load was the percentage of DNA quantification of the hydrogen peroxide-added dark group, the hydrogen peroxide-free light irradiation group and the hydrogen peroxide-added light irradiation group to DNA quantification of the hydrogen peroxide-free dark group.

As shown in FIG. 2, compared to the hydrogen peroxide-free dark group, the relative viral load of HCV of the hydrogen peroxide-added dark group was reduced by about 40%, showing that without light irradiation step, the atomized particles obtained by the water-soluble photosensitive composition added with 0.03 wt % of hydrogen peroxide were able to reduce the pathogenicity of HCV. Secondly, the relative viral load of the hydrogen peroxide-free light irradiation group and that of the hydrogen peroxide-added light irradiation group were almost 0%. It was confirmed that whether or not 0.03 wt % of hydrogen peroxide was added when the light dose was high (20 J/cm$^2$), the photoactivated atomized particles obtained by subjecting the water-soluble photosensitive composition to the light irradiation step could make HCV almost lose its pathogenicity.

As shown in FIG. 3, compared to the hydrogen peroxide-free dark group, the relative viral load of DENV of the hydrogen peroxide-added dark group was reduced by about 50%, showing that without light irradiation step, the atomized particles obtained by the water-soluble photosensitive composition added with 0.03 wt % of hydrogen peroxide were able to reduce the pathogenicity of DENV. Secondly, the relative viral load of the hydrogen peroxide-free light irradiation group and that of the hydrogen peroxide-added light irradiation group were almost 0%. It was confirmed that whether or not 0.03 wt % of hydrogen peroxide was added, when the light dose was high (20 J/cm$^2$), the photoactivated atomized particles obtained by subjecting the water-soluble photosensitive composition with the light irradiation step could make DENV almost lose its pathogenicity.

3. Effect of Light Dose on Environmental Disinfection Efficacy.

The water-soluble photosensitive composition of Preparation Example 2 (hydrogen peroxide-free) was subjected to an atomization step for 150 seconds to obtain atomized particles, and the atomized particles were respectively subjected to a light irradiation step with different light doses (0 J/cm$^2$, 10 J/cm$^2$, 20 J/cm$^2$), thereby obtaining photoactivated atomized particles, in which 0 J/cm$^2$ meant that the light irradiation step was not carried out. The relative viral load was then detected by Q-PCR.

Figure 4:
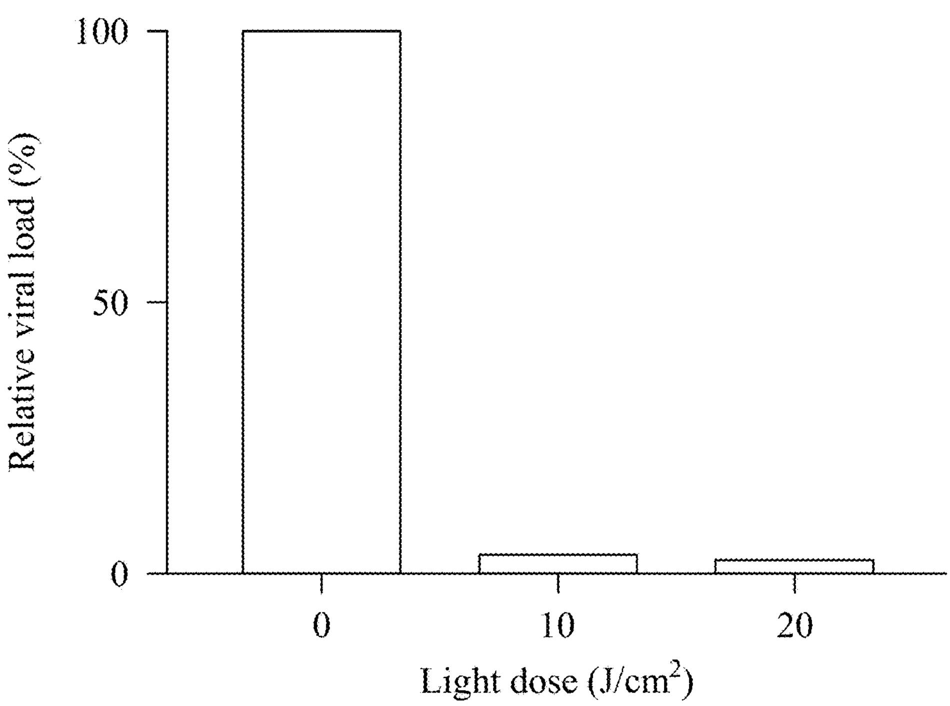
FIG. 4 is a histogram of the relative toxicity of different light doses to HCV according to an embodiment of the present invention.
Figure 5:
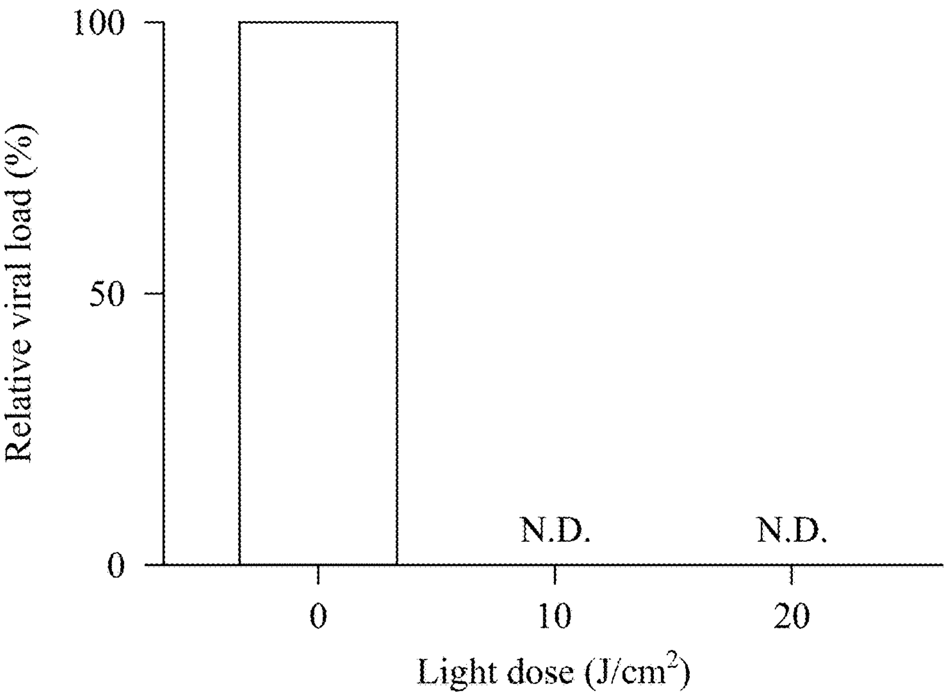
FIG. 5 is a histogram of the relative toxicity of different light doses to DENV according to an embodiment of the present invention.

Please refer to FIG. 4 and FIG. 5, in which FIG. 4 was a histogram of the relative toxicity of different light doses to HCV according to an embodiment of the present invention, and FIG. 5 was a histogram of the relative toxicity of different light doses to DENV according to an embodiment of the present invention. As shown in FIG. 4 and FIG. 5, the horizontal axes represented the light dose (unit: J/cm$^2$), and the vertical axes represented the relative viral load (unit: %), in which the quantification of viral DNA in the virus solution that was treated with the atomized particles not subjected to the light irradiation step (the light dose was 0 $J/cm^2$) was taken as 100% for the relative viral load, and N.D. (non-detectable) indicated to be lower than the detection limit.

As shown in FIG. 4, the photoactivated atomized particles subjected to the light irradiation step with the light doses of 10 $J/cm^2$ and 20 $J/cm^2$ of white light could significantly reduce the relative viral load of HCV. As shown in FIG. 5, the photoactivated atomized particles subjected to the light irradiation step with the light doses of 10 $J/cm^2$ and 20 $J/cm^2$ of white light could make the relative viral load of DENV to be almost 0. It can be seen from FIG. 4 and FIG. 5 that the light doses of 10 $J/cm^2$ and 20 $J/cm^2$ of white light could effectively reduce the pathogenicity of the enveloped viruses.

4. Effect of Low Light Dose and Different Atomization Times on Environmental Disinfection Efficacy.

Disinfection efficacy of the photoactivated atomized particles subjected to the atomization step with different atomization times and the light irradiation step with the low light dose (2.5 $J/cm^2$) on the water-soluble photosensitive composition of Preparation Example 2 (hydrogen peroxide-free) to non-enveloped viruses in the environment was evaluated, in which the atomization time was 15 seconds, 30 seconds, 75 seconds or 150 seconds. Next, the pathogenicity of bacteriophage MS2 was detected by a plaque assay, which was briefly described as follows: host cells (*Escherichia coli*) were cultivated in a bacterial culture plate, and the virus solution and the host cells were then added to an agar culture plate and mixed to co-culture the virus and the host cells for 1 day. Next, the number of lysed plaques on the agar culture plate was calculated to evaluate the virulence of the virus, in which the higher number of the lysed plaques indicated a higher virulence of the virus, that is, higher pathogenicity.

Figure 6:
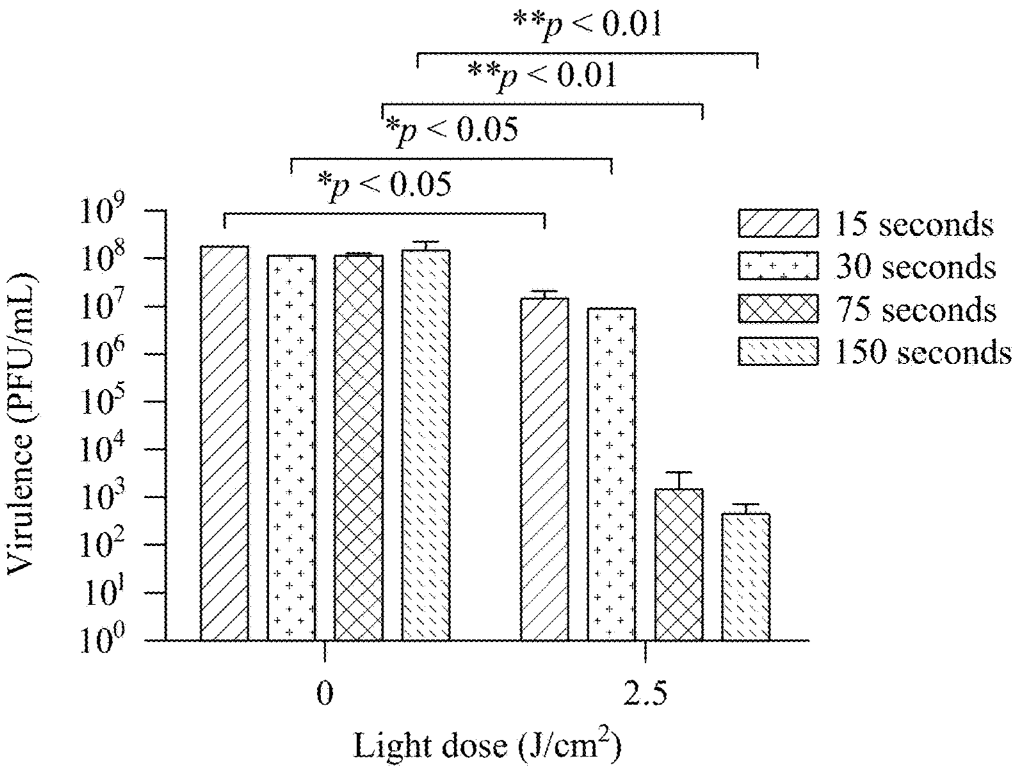
FIG. 6 is a histogram of the virulence of bacteriophage MS2 subjected to a light irradiation step of a low light dose and different atomization times according to an embodiment of the present invention.

Please refer to FIG. 6, which was a histogram of the virulence of bacteriophage MS2 subjected to a light irradiation step of a low light dose and different atomization times according to an embodiment of the present invention, in which the horizontal axis represented the light dose (unit: $J/cm^2$), and the vertical axis represented the virulence of bacteriophage MS2 (unit: plaque forming units (PFU)/mL), and the straight bars represented 15 seconds, 30 seconds, 75 seconds or 150 seconds from left to right.

As shown in FIG. 6, in the absence of the light irradiation step (i.e., the light dose was 0 $J/cm^2$), the virulence of bacteriophage MS2 was about 108 PFU/mL regardless of whether the atomization step was performed for 15 seconds, 30 seconds, 75 seconds or 150 seconds. Secondly, compared to those not subjected to the light irradiation step, the photoactivated atomized particles subjected to the light irradiation step and the atomization step for 15 seconds could significantly reduce the virulence of bacteriophage MS2. Furthermore, the longer the atomization time was, the better the effect of the obtained photoactivated atomized particles on reducing the virulence of bacteriophage MS2 was, and the photoactivated atomized particles subjected to the atomization step for 75 seconds could reduce the virulence of bacteriophage MS2 by 105 PFU/mL (equivalent to 5 logarithms, 5 logs). It may be seen that when the atomization step was within 2 minutes, the obtained photoactivated atomized particles could reduce the pathogenicity of bacteriophage MS2 by 99.999% (equivalent to 5 logarithms, 5 logs), and the effect of the obtained photoactivated atomized particles was much greater than the standard of the "good environmental disinfection efficacy" described in the description (the pathogenicity of pathogens was reduced by at least 99.9% (the US standard) or 99.99% (the EU standard).

In general, compared to the enveloped viruses, the pathogenicity and/or the infectivity of the non-enveloped viruses were less affected by photodynamic disinfection. However, the aforementioned experimental results confirmed that the photoactivated atomized particles subjected to the atomization step for 75 seconds could inhibit the pathogenicity of the non-enveloped bacteriophage MS2 by 99.999%, indicating that the above method should be more effective in inhibiting enveloped viruses (e.g., SARS-COV-2 virus that causes COVID-19), i.e., the results suggested that the above method could inhibit more than 99.999% of the enveloped viruses.

5. Disinfection Effect of Atomized Particles and Photoactivated Atomized Particles on Viruses in Ambient Air.

The air containing 108 PFU/mL (untreated group) of bacteriophage MS2 (so-called MS2 virus) was compressed and added to the aforementioned airtight box for 30 minutes. Next, the water-soluble photosensitive composition of Preparation Example 1 (containing hydrogen peroxide) was subjected to an atomization step with an ultrasonic atomizer, so as to treat the MS2 virus in the air with the atomized particles. The MS2 virus in the airtight box at this time was collected to detect the virulence of the MS2 virus of an atomized particle treatment group. Next, LED red light (wavelength: 644 nm; light intensity: 30 $mW/cm^2$) was turned on at a distance of 30 centimeters from the airtight box to perform a light irradiation step on the atomized particles, followed by treating the atomized particles with a light dose of 10 $J/cm^2$ to obtain photoactivated atomized particles. Next, the MS2 virus in the air was treated with the photoactivated atomized particles. The MS2 virus in the airtight box was collected to detect the virulence of the MS2 virus of a photoactivated atomized particle treatment group.

Figure 7:
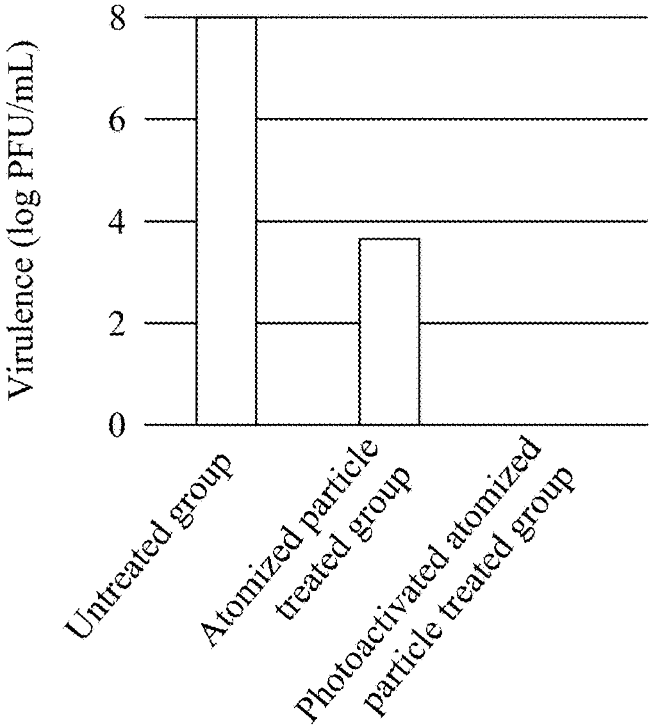
FIG. 7 is a histogram of the virulence of bacteriophage MS2 in air treated with atomized particles or photoactivated atomized particles according to an embodiment of the present invention.
Figure 8A:
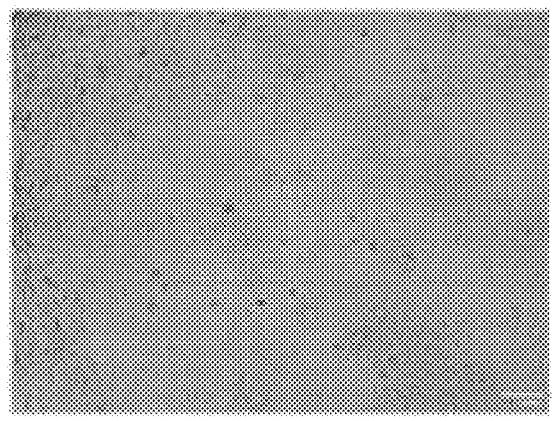
FIG. 8A, FIG. 8B, FIG. 9A, FIG. 9B, FIG. 10A, FIG. 10B, FIG. 11A and FIG. 11B show microscopic images of visible light (FIG. 8A, FIG. 9A, FIG. 10A, and FIG. 11A) and fluorescence (FIG. 8B, FIG. 9B, FIG. 10B, and FIG. 11B) of host cells in a blank group (FIG. 8A, FIG. 8B), a methylene blue-free dark group (FIG. 9A, FIG. 9B), a methylene blue-added dark group (FIG. 10A, FIG. 10B), and a methylene blue-added light radiation group (FIG. 11A, FIG. 11B) according to the present invention.
Figure 8B:

Please refer to FIG. 7, which was a histogram of the virulence of bacteriophage MS2 in air treated with atomized particles or photoactivated atomized particles according to an embodiment of the present invention, in which the horizontal axis represented the groups, from left to right were the untreated group, the atomized particle treatment group and the photoactivated atomized particle treatment group, and the vertical axis represented the virulence (unit: log PFU/mL). As shown in FIG. 7, compared to the untreated group, the virulence of the atomized particle treatment group was reduced by 104 PFU/mL, indicating that the atomized particles could reduce the pathogenicity of the virus in the air by about 99.99%. Secondly, the virulence of the photoactivated atomized particle treatment group was almost 0, indicating that the photoactivated atomized particles could reduce the pathogenicity of the virus in the air by about 99.999999%, and had a good disinfection effect on the virus in the air in the environment.

6. Environmental Disinfection Efficacy of Photoactivated Atomized Particles Inhibiting SARS-COV-2.

Studies had found that SARS-Cov-2 infected host cells by binding the spike glycoprotein (S protein) to the angiotensin-converting enzyme (ACE) 2 receptor of human (host) cells. Therefore, the following experiment used a lentivirus that expressed the S protein of SARS-COV-2 (purchased from ACE Biolabs, Taiwan; Item No.: PV031) as pseudovirus of SARS-COV-2 to evaluate the effect of photodynamic disinfection on reducing the infectivity of SARS-COV-2, in which the pseudovirus of SARS-COV-2 was able to express a gene fragment of green fluorescent protein (GFP), so that the infected host cells could exhibit green fluorescence under blue light (wavelength of 488 nm). The infectivity of the pseudovirus of SARS-COV-2 was evaluated by counting the number of the host cells exhibiting green fluorescence. It was supplemented that the host cells used in the following experiments were HEK293 cells that were able to express ACE2, that is, ACE2-3×FLAG-HEK293T cells, which were purchased from ACE Biolabs, Taiwan; product number: CL0021.

The host cells were cultured with a cell culture medium to obtain a cell culture of 200 cells/μL. 50 μL of the cell culture was added to each well of a black 96-well cell culture plate. The aforementioned cell culture was phenol red-free Dulbecco's modified Eagle medium (DMEM) contained 10 vol % of fetal bovine serum (FBS), 1 vol % of penicillin/streptomycin (P/S) solution, 3 μg/mL of puromycin.

Next, the virus solution was added to each well of the 96-well cell culture plate for co-cultivation at 37° C. for 48 hours. The host cells in a blank group were not treated with a virus solution. The virus solution of a methylene blue-free dark group was not treated with the atomized particles or the photoactivated atomized particles. The virus solution of a methylene blue-added dark group was treated with the atomized particles, and the atomized particles were obtained by performing the atomization step on the water-soluble photosensitive composition (hydrogen peroxide-free) for 75 seconds. The virus solution of a methylene blue-added light irradiation group was treated with the photoactivated atomized particles, which the photoactivated atomized particles were obtained by performing the atomization step on the water-soluble photosensitive composition (hydrogen peroxide-free) of Preparation Example 2 for 75 seconds and the light irradiation step of 2.5 J/cm$^2$.

Please refer to FIG. 8A, FIG. 8B, FIG. 9A, FIG. 9B, FIG. 10A, FIG. 10B, FIG. 11A and FIG. 11B, which showed microscopic images of visible light (FIG. 8A, FIG. 9A, FIG. 10A, and FIG. 11A) and fluorescence (FIG. 8B, FIG. 9B, FIG. 10B, and FIG. 11B) of the host cells in the blank group (FIG. 8A, FIG. 8B), the methylene blue-free dark group (FIG. 9A, FIG. 9B), the methylene blue-added dark group (FIG. 10A, FIG. 10B), and the methylene blue-added light radiation group (FIG. 11A, FIG. 11B) according to the present invention.

Figure 9A:
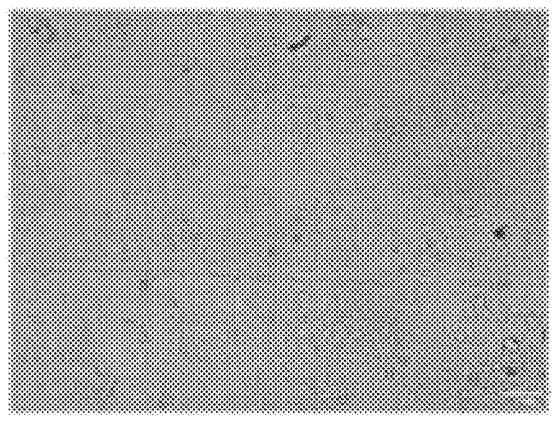
Figure 9B:
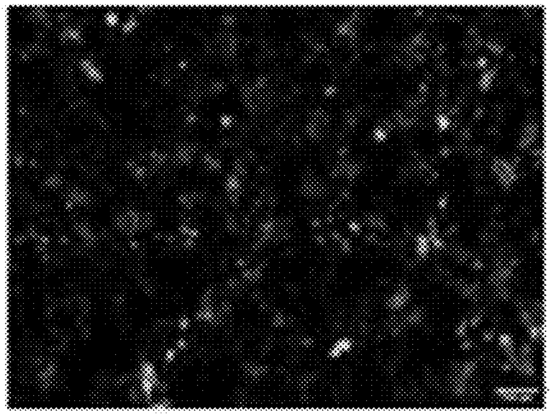
Figure 10A:
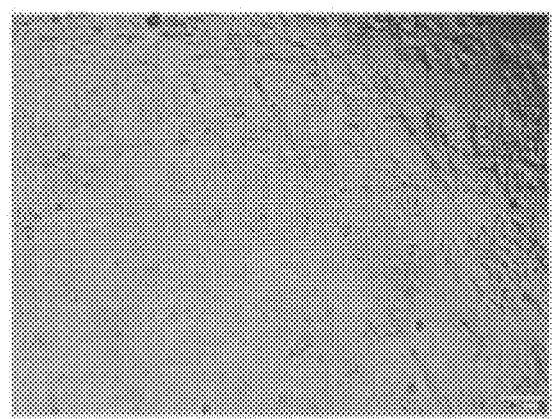
Figure 10B:
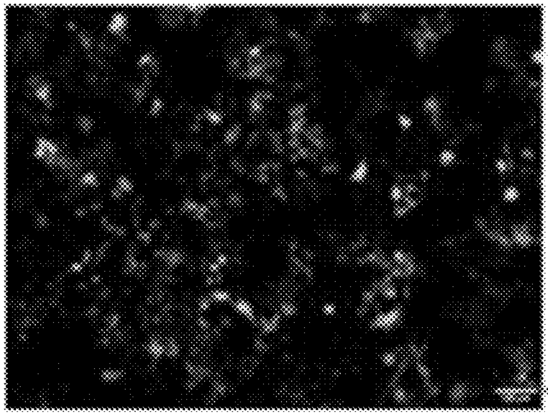
Figure 11A:
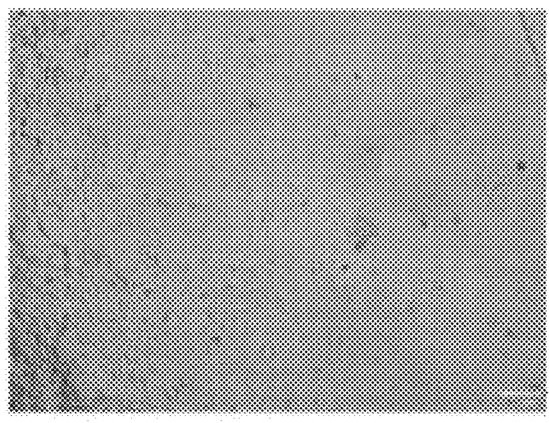
Figure 11B:

As shown in FIG. 9B and FIG. 10B, the host cells of the methylene blue-free dark group and the methylene blue-added dark group exhibited green fluorescence, but as shown in FIG. 11B, the host cells of the methylene blue-added light irradiation group did not exhibit green fluorescence, confirming that the photoactivated atomized particles were able to effectively reduce the infectivity of pseudovirus of SARS-COV-2, in which the photoactivated atomized particles were obtained by subjecting the water-soluble photosensitive composition to the atomization step for 75 seconds and the light irradiation step of 2.5 J/cm$^2$.

Please refer to FIG. 12, which was a histogram of quantified relative fluorescence intensity of host cells in FIG. 9B, FIG. 10B and FIG. 11B, in which the horizontal axis represented the group, which were the methylene blue-free dark group, the methylene blue-added dark group and the methylene blue-added light radiation group, and the vertical axis represented the relative fluorescence intensity (unit: %) taking the fluorescence intensity of the methylene blue-free dark group as 100%.

As shown in FIG. 12, compared to the methylene blue-free dark group and the methylene blue-added dark group, the host cells of the methylene blue-added light irradiation group exhibited almost no green fluorescence, indicating that the host cells of the methylene blue-added light irradiation group were barely infected with pseudovirus of SARS-COV-2, confirming that the photoactivated atomized particles were able to effectively reduce the infectivity of pseudovirus of SARS-CoV-2, which the photoactivated atomized particles were obtained by subjecting the water-soluble photosensitive composition to the atomization step for 75 seconds and the light irradiation step of 2.5 J/cm$^2$.

7. Effect of Extremely Low Light Dose on Environmental Disinfection Efficacy.

Gloves were sterilized, and 90 μL of the virus solution was spread on the surfaces of the gloves, in which the virus solution was prepared with PBS and contained 108 PFU of bacteriophage MS2. The gloves were divided into a methylene blue-untreated group and a methylene blue-treated group, in which no treatment was performed on the gloves of the methylene blue-untreated group, and 10 μL of the water-soluble photosensitive composition of Preparation Example 2 was spread on the gloves of the methylene blue-treated group. Next, red light with a light intensity of 32.8 mW/cm$^2$ was irradiated on the glove surfaces for 0 seconds (the light dose was 0 J/cm$^2$), 9 seconds (the light dose was 0.3 J/cm$^2$) and 19 seconds (the light dose was 0.6 J/cm$^2$), and the aforementioned plaque assay was used to detect the pathogenicity of bacteriophage MS2.

Figure 13:
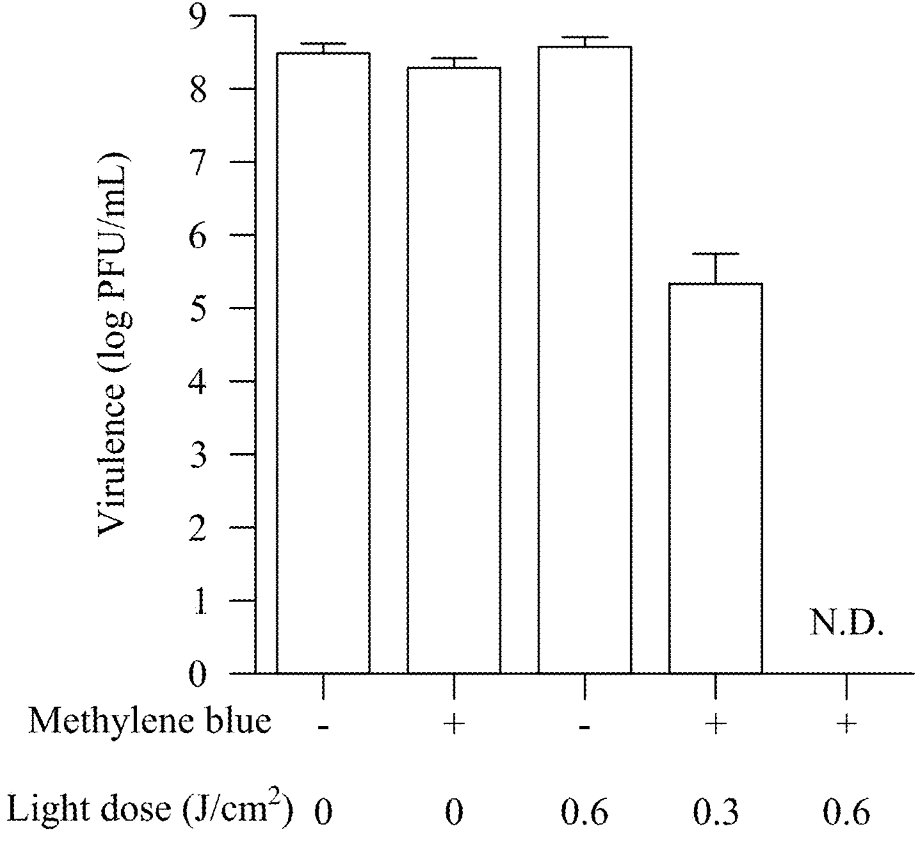
FIG. 13 is a histogram of the virulence of bacteriophage MS2 on gloves of different groups after a low light dose irradiation step according to an embodiment of the present invention.

Please refer to FIG. 13, which was a histogram of the virulence of bacteriophage MS2 of the gloves of the different groups after the light irradiation step of the low light dose according to an embodiment of the present invention, in which the horizontal axis represented the addition of methylene blue or not and the light dose (unit: J/cm$^2$), the symbol "−" indicated the methylene blue-untreated group, the symbol "+" indicated the methylene blue-treated group, and the vertical axis represented the virulence (unit: log PFU/mL), and N.D. (non-detectable) indicated to be lower than a detection limit.

As shown in FIG. 13, after the gloves of the methylene blue-untreated group were subjected to the red light irradiation step with the light dose of 0.3 J/cm$^2$, the virulence of bacteriophage MS2 was reduced by 99.9% (equivalent to 3 logarithms, 3 logs), and when the gloves were subjected to the light dose of 0.6 J/cm$^2$, the virulence of bacteriophage MS2 was reduced by 99.999999% to 99.9999999% (equivalent to 8 to 9 logarithms, 8 logs to 9 logs), confirming that the lower light dose was also effective for environmental disinfection.

It was supplemented that, as shown in FIG. 2, the atomized particles obtained by the water-soluble photosensitive composition of Preparation Example 1 not subjected to the light irradiation step were able to reduce the relative viral load by about 40%. Therefore, it can be inferred from FIG. 2 and FIG. 13 that the photoactivated atomized particles obtained by the method of photodynamic environmental disinfection of the present invention with the lower light dose could reduce the pathogenicity and/or the infectivity of viruses by at least 99.99%.

In summary, the advantages of the method of photodynamic environmental disinfection of the present invention are that the water-soluble photosensitive composition is composed of low-dose (greater than 0 mM to 0.005 mM) of methylene blue and low-dose (greater than 0 wt % to 0.05 wt %) of hydrogen peroxide and water, and after the atomization step for the short time (50 seconds to 100 seconds) and the low light dose (0.01 J/cm$^2$ to 300 J/cm$^2$) are performed, the obtained photoactivated atomized particles are able to reduce the pathogenicity and/or the infectivity of viruses by at least 99.99%.

In a word, although the present invention uses specific compositions, specific viruses, specific equipment, specific disinfection procedures and specific evaluation methods as examples to illustrate the water-soluble photosensitive composition of photodynamic environmental disinfection and method of using the same, the person having ordinary skill in the art of the present invention should understand that the present invention is not limited thereto. Without departing from the spirit and scope of the present invention, the present invention can also use other components, other viruses, other equipment, other disinfection procedures and other evaluation methods.

Although the present invention has been disclosed above with several specific embodiments, various modifications, changes and replacements can be made to the foregoing disclosure, and it should be understood that, without departing from the spirit and scope of the present invention, in some cases, some features of the embodiments of the present invention will be used but other features will not be used correspondingly. Therefore, the spirit of the present invention and the scope of claims should not be limited to those described in the above exemplary embodiments.

What is claimed is:

1. A method of photodynamic environmental disinfection, comprising:

performing an atomization step on a water-soluble photosensitive composition to obtain atomized particles in space, wherein the water-soluble photosensitive composition is consisting of methylene blue of more than 0 mM and equal to or less than 50 mM, hydrogen peroxide ($H_2O_2$) of more than 0 wt % to 1 wt %, and a balanced amount of water;

performing a light irradiation step using white light of 0.01 J/cm$^2$ to 300 J/cm$^2$ on the atomized particles for a time of irradiation to obtain photoactivated atomized particles; and applying the photoactivated atomized particles to a surface of an object and/or air of the space, wherein compared to the surface of the object and/or the air of the space where the photoactivated atomized particles are not applied, pathogenicity and/or infectivity of viruses on the surface of the object and/or in the air of the space where the photoactivated atomized particles are applied is reduced by at least 99.99%.

2. The method of photodynamic environmental disinfection of claim 1, wherein the atomization step is performed at a rate of 0.1 mL to 150 mL per minute.

3. The method of photodynamic environmental disinfection of claim 1, wherein the atomization step is performed for 1 second to 300 seconds.

4. The method of photodynamic environmental disinfection of claim 1, wherein a particle size of each of the atomized particles is 0.1 μm to 100 μm.

5. The method of photodynamic environmental disinfection of claim 1, wherein a total volume ratio of the space to each of the atomized particles is 1:0.0001 to 1:0.01.

6. The method of photodynamic environmental disinfection of claim 1, wherein a light source of the white light is selected from the group consisting of natural light, a light-emitting diode, a fluorescent lamp, a halogen lamp, an incandescent lamp, a laser, and any combination thereof.

7. The method of photodynamic environmental disinfection of claim 1, wherein a wavelength of the white light comprises 400 nm to 760 nm.

8. The method of photodynamic environmental disinfection of claim 1, wherein the viruses are selected from the group consisting of Flaviviridae, Fiersviridae, Coronaviridae and any combination thereof.

9. The method of photodynamic environmental disinfection of claim 1, wherein the viruses are selected from the group consisting of hepatitis C virus (HCV), dengue virus (DENV), MS2 bacteriophage, severe acute respiratory syndrome coronavirus 2 (SARS-COV-2) and any combination thereof.

10. A method of an environmental disinfection with a water-soluble photosensitive composition, comprising:

performing an atomization step on a water-soluble photosensitive composition to obtain atomized particles in space at a rate of 0.1 mL to 150 mL per minute for 1 second to 300 seconds, wherein the water-soluble photosensitive composition is consisting of methylene blue of greater than 0 mM and equal to or less than 50 mM, hydrogen peroxide of greater than 0 wt % to 1 wt % and a balanced amount of water;

performing a light irradiation step using white light of 0.01 J/cm$^2$ to 300 J/cm$^2$ on the atomized particles to obtain photoactivated atomized particles; and applying the photoactivated atomized particles to a surface of an object and/or air of space, wherein compared to the surface of the object and/or the air of the space where the photoactivated atomized particles are not applied, pathogenicity and/or infectivity of viruses on the surface of the object and/or in the air of the space where the photoactivated atomized particles are applied is reduced by at least 99.99%.

11. The method of the environmental disinfection with the water-soluble photosensitive composition of claim 10, wherein a particle size of each of the atomized particles is 0.1 μm to 100 μm.

12. The method of the environmental disinfection with the water-soluble photosensitive composition of claim 10, wherein the viruses are selected from the group consisting of Flaviviridae, Fiersviridae, Coronaviridae and any combination thereof.

13. The method of the environmental disinfection with the water-soluble photosensitive composition of claim 10, wherein the viruses are selected from the group consisting of hepatitis C virus (HCV), dengue virus (DENV), MS2 bacteriophage, severe acute respiratory syndrome coronavirus 2 (SARS-COV-2) and any combination thereof.

14. The method of the environmental disinfection with the water-soluble photosensitive composition of claim 10, wherein a total volume ratio of the space to each of the atomized particles are 1:0.0001 to 1:0.01.

15. The method of the environmental disinfection with the water-soluble photosensitive composition of claim 10, wherein a light source of the white light is selected from the group consisting of natural light, a light-emitting diode, a fluorescent lamp, a halogen lamp, an incandescent lamp, a laser, and any combination thereof.

16. The method of the environmental disinfection with the water-soluble photosensitive composition of claim 10, wherein a wavelength of the white light comprises 400 nm to 760 nm.

* * * * *